US010758336B2

(12) United States Patent
Xu et al.

(10) Patent No.: US 10,758,336 B2
(45) Date of Patent: Sep. 1, 2020

(54) DECELLULARIZED MUSCLE MATRIX

(71) Applicant: LifeCell Corporation, Branchburg, NJ (US)

(72) Inventors: Hui Xu, Plainsboro, NJ (US); Hua Wan, Princeton, NJ (US); I-Chien Liao, Princeton, NJ (US)

(73) Assignee: LifeCell Corporation, Madison, NJ (US)

( * ) Notice: Subject to any disclaimer, the term of this patent is extended or adjusted under 35 U.S.C. 154(b) by 217 days.

(21) Appl. No.: 14/410,204

(22) PCT Filed: Jul. 1, 2013

(86) PCT No.: PCT/US2013/048915
§ 371 (c)(1),
(2) Date: Dec. 22, 2014

(87) PCT Pub. No.: WO2014/008181
PCT Pub. Date: Jan. 9, 2014

(65) Prior Publication Data
US 2015/0282925 A1    Oct. 8, 2015

Related U.S. Application Data

(60) Provisional application No. 61/668,584, filed on Jul. 6, 2012.

(51) Int. Cl.
*A61F 2/08* (2006.01)
*A61L 27/36* (2006.01)
*A61K 35/34* (2015.01)

(52) U.S. Cl.
CPC .......... *A61F 2/08* (2013.01); *A61K 35/34* (2013.01); *A61L 27/362* (2013.01); *A61L 27/3604* (2013.01); *A61L 27/367* (2013.01); *A61L 27/3687* (2013.01); *A61F 2002/0894* (2013.01); *A61F 2240/001* (2013.01); *A61L 2400/06* (2013.01); *A61L 2430/30* (2013.01); *A61L 2430/40* (2013.01)

(58) Field of Classification Search
CPC .......... A61L 2400/06; A61L 2430/40; A61L 27/3604; A61L 27/3683; A61L 2430/30; A61L 27/367; A61F 2/02; A61F 2002/0894; A61F 2/08; A61K 35/34
See application file for complete search history.

(56) References Cited

U.S. PATENT DOCUMENTS

| | | |
|---|---|---|
| 5,336,616 A | 8/1994 | Livesey et al. |
| 5,364,756 A | 11/1994 | Livesey et al. |
| 6,166,288 A | 12/2000 | Diamond et al. |
| 6,381,026 B1 | 4/2002 | Schiff et al. |
| 6,933,326 B1 | 8/2005 | Griffey et al. |
| 7,166,477 B2 * | 1/2007 | Prusiner .................. C12Q 1/24 435/1.1 |
| 7,358,284 B2 | 4/2008 | Griffey et al. |
| 7,883,541 B2 | 2/2011 | Mills et al. |
| 2002/0128724 A1* | 9/2002 | Ollerenshaw ............. A61F 2/04 623/23.71 |
| 2003/0035843 A1 | 2/2003 | Livesey et al. |
| 2003/0143207 A1 | 7/2003 | Livesey et al. |
| 2005/0028228 A1 | 2/2005 | McQuillan et al. |
| 2006/0073592 A1 | 4/2006 | Sun et al. |
| 2006/0127375 A1 | 6/2006 | Livesey et al. |
| 2006/0210960 A1 | 9/2006 | Livesey et al. |
| 2007/0009586 A1 | 1/2007 | Cohen et al. |
| 2007/0078522 A2* | 4/2007 | Griffey ................ A61K 9/0024 623/23.76 |
| 2007/0248575 A1 | 10/2007 | Connor et al. |
| 2008/0027562 A1 | 1/2008 | Fujisato et al. |
| 2009/0130221 A1 | 5/2009 | Bolland et al. |
| 2009/0306790 A1 | 12/2009 | Sun |
| 2010/0233235 A1 | 9/2010 | Matheny et al. |
| 2011/0021753 A1 | 1/2011 | Huang |
| 2011/0054588 A1 | 3/2011 | Xu et al. |
| 2012/0010728 A1 | 1/2012 | Sun et al. |
| 2012/0276213 A1 | 11/2012 | Chen |
| 2014/0004549 A1 | 1/2014 | Chen et al. |
| 2014/0088701 A1 | 3/2014 | Sun et al. |
| 2014/0377833 A1 | 12/2014 | Chen et al. |

FOREIGN PATENT DOCUMENTS

| | | | | |
|---|---|---|---|---|
| WO | WO-2006095342 A2 * | 9/2006 | ......... | A61L 27/3873 |
| WO | WO2007110634 | * 10/2007 | ............. | A61L 27/36 |
| WO | WO-2013096249 A1 * | 6/2013 | ............. | A61L 27/36 |

OTHER PUBLICATIONS

Stern et al. The influence of extracellular matrix derived from skeletal muscle tissue on the proliferation and differentiation of myogenic progenitor cells ex vivo. Biomaterials. 2009;30:2393-2399.*

Crapo et al. An overview of tissue and whole organ decellularization processes. Biomaterials. 2011;32(12):3233-3243.*

Bellows et al. Abdominal wall repair using human acellular dermis. The American Journal of Surgery. 2007;194:192-198.*

Spicer et al. Fibrin glue as a drug delivery system. J Control Release. 2010;148(1):49-55.*

Badylak et al., "Extracellular matrix as a biological scaffold material: Structure and function," Acta Biomaterials, vol. 5, pp. 1-13, 2009.

Collins et al., "Cardiac Xenografts Between Primate Species Provide Evidence for the Importance of the α-Galactosyl Determinant in Hyperacute Rejection," J. Immunol., vol. 154, pp. 5500-5510, 1995.

(Continued)

*Primary Examiner* — Lynn Y Fan
(74) *Attorney, Agent, or Firm* — McCarter & English, LLP

(57) ABSTRACT

Disclosed herein are muscle implants and methods of making muscle implants comprising one or more decellularized muscle matrices. The muscle matrices can, optionally, be joined to one or more decellularized dermal matrices. The muscle implants can be used to enhance muscle volume or to treat muscle damage, defects, and/or disorders. The decellularized muscle matrices in the implants retain at least some of the myofibers found in a muscle tissue prior to processing.

12 Claims, 7 Drawing Sheets

(56) References Cited

OTHER PUBLICATIONS

Dequach et al.; "Injectable skeletal muscle matrix hydrogel promotes neovascularization and muscle cell infiltration in a hindlimb ischemia model—NIH Public Access;" Eur. Cell Mater.; 23:400-412 (Jun. 5, 2013).

Dobrin et al., "Elastase, collagenase, and the biaxial elastic properties of dog carotid artery," Am. J. Physiol. Heart Circ. Physiol., vol. 247, pp. H124-H131, 1984.

Galili et al., "Interaction between Human Natural Anti-$\alpha$-Galactosyl Immuglobulin G and Bacteria of the Human Flora," Infection and Immunity, vol. 56, pp. 1730-1737, 1988.

Galili et al., "Man, Apes, and Old World Monkeys Differ from other Mammals in the Expression of a-Galctosyl Epitopes on Nucleated Cells," Journal of Biological Chemistry, vol. 263, No. 33, pp. 17755-17762, 1988.

Galili, Uri, "Interaction of the natural anti-Gal antibody with $\alpha$-galactosyl epitopes: a major obstacle for xenotransplantation in humans," Immunology Today, vol. 14, pp. 480-482, 1993.

Good et al., "Identification of Carbohydrate Structures That Bind Human Antiporcine Antibodies: Implications for Discordant Xenografting in Humans," Transplant Proc., vol. 24, pp. 559-562, 1992.

Hamadeh et al., "Human Natural Anti-Gal IgG Regulates Alternative Complement Pathway Activation on Bacterial Surfaces," J. Clin. Invest., vol. 89, pp. 1223-1235, 1992.

Ionescu et al., "Effect of Papain and Bromelin on Muscle and Collagen Proteins in Beef Meat," The Annals of the University Dunarea de Jos of Galati, Fasccile VI, Food Technology, New Series, pp. 9-16, 2008.

Karlinsky et al., "In Vitro Effects of Elastase and Collagenase on Mechanical Properties of Hamster Lungs," Chest, vol. 69, No. 2, pp. 275-276, 1976.

Lu et al., "Novel porous aortic elastin and collagen scaffolds for tissue engineering," Biomaterials, vol. 25, No. 22, pp. 5227-5237, 2004.

Merritt et al., "Functional Assessment of Skeletal Muscle Regeneration Utilizing Homologous Extracellular Matrix as Scaffolding," Tissue Engineering, vol. 16, No. 4, Part A, pp. 1395-1405, 2010.

Reihsner et al., "Biomechanical properties of elastase treated palmar aponeuroses," Connective Tissue Research, Vo. 26, pp. 77-86, 1991.

Sandrin et al., Anti-pig IgM antibodies in human serum react predominantly with Gal($\alpha$1-3)Gal epitopes, Proc. Natl. Acad. Sci., vol. 90, pp. 11391-11395, 1993.

Stern et al.; "The influence of extracellular matrix drived from skeletal muscle tissue on the proliferation and differentiation of myogenic progenitor cells ex vivo;" Biomaterials—Elsevier Science Publishers; 30(12):2393-2399 (Apr. 1, 2009).

Tedder et al., "Stabilized Collagen Scaffolds for Heart Valve Tissue Engineering," Tissue Engineering, vol. 00, Part A, pp. 1-12, 2008.

Turner et al., "Regeneration of skeletal muscle," Cell Tissue Res, vol. 347, No. 3, pp. 759-774, 2012.

Valentin, et al., "Functional skeletal muscle formation with a biologic scaffold," Biomaterials, vol. 31, No. 9, pp. 7475-7484, 2010.

Wolf et al.; "Biologic scaffold composed of skeletal muscle extracellular matrix:" Biomaterials—Elsevier Science Publishers; 33(10):2916-2925 (Dec. 31, 2011).

Xu et al., "A Porcine-Derived Acellular Dermal Scaffold That Supports Soft Tissue Regeneration: Removal of Terminal Galactose-$\alpha$-(1,3)-Galactose and Retention of Matrix Structure," Tissue Engineering, vol. 15, pp. 1-13, 2009.

Yuan et al., "Effects of collagenase and elastase on the mechanical properties of lung tissue strips," J. App. Physiol., Vo. 89, pp. 3-14, 2000.

Gamba PG et al, "Experimental abdominal wall defect repaired with acellular matrix," Pediatr Surg Int. (2002) 18(5-6):327-331.

De Coppi P. et al., "Myoblast-acellular skeletal muscle matrix constructs guarantee a long-term repair of experimental full-thickness abdominal wall defects," Tissue Eng. Jul. 2006;12(7):1929-36.

Conconi MT et al. "In vitro and in vivo evaluation of acellular diaphragmatic matrices seeded with muscle precursorscells and coated with VEGF silica gels to repair muscle defect of the diaphragm", J Biomed Mater Res A. May 2009;89(2):304-16.

\* cited by examiner

DECELLULARIZED MUSCLE MATRIX

This application is a 35 U.S.C. § 371 national stage filing of International Application No. PCT/US2013/048915, filed on Jul. 1, 2013, which claims the benefit of priority under 35 U.S.C. § 119 to U.S. Provisional Application No. 61/668,584, filed on Jul. 6, 2012, the content of each of which is incorporated herein by reference in its entirety.

The present disclosure relates generally to methods of making and using decellularized muscle matrices in the repair, regeneration, and/or treatment of abdominal wall and other muscle defects.

Various injuries, diseases, and surgical procedures result in the loss of muscle mass, particularly skeletal muscle. For example, surgical removal of soft tissue sarcomas and osteosarcomas can result in the loss of bulk muscle. Other surgical and cosmetic procedures, such as hernia repair and muscle augmentation, require long-term management of muscle content. Muscle damage can also result from injury, such as from blunt force trauma and gunshot injuries.

Current muscle regenerative procedures focus on the use of muscle allografts (e.g., harvesting gluteus maximus muscle from donor sites on the patient or from a cadaver), and the use of xenografts comprising completely decellularized dermal and other tissue matrices. However, the use of muscle transplants can lead to excess inflammation (resulting in scar tissue formation and potential rejection) and, if harvested from the patient, presents the problem of muscle loss at the donor site. Likewise, completely decellularized matrices can lose strength over time and are more effective for the repair of fascia than for the overlying muscle. Thus, a need remains for improved methods and compositions for the long-term management of muscle repair and regeneration.

Accordingly, disclosed herein are muscle implants comprising decellularized muscle matrices that retain at least some of the myofibers normally found in a muscle tissue prior to processing, and their use to improve muscle repair, treatment, enhancement, and/or regeneration. In various embodiments, a method of preparing a muscle implant is provided, comprising providing at least one muscle sample; contacting the at least one muscle sample with a trypsin solution; decellularizing the at least one muscle sample to produce at least one decellularized muscle matrix; and controlling the exposure duration and/or concentration of the trypsin solution in order to retain at least some of the myofibers normally found in the muscle sample prior to decellularization. In some embodiments, the decellularization solution comprises at least one of TRITON X-100™, sodium dodecyl sulfate, sodium deoxycholate, and polyoxyethylene (20) sorbitan monolaurate. In some embodiments, the decellularized muscle matrix retains about 20-80% of the myofibers normally found in the muscle tissue prior to processing. In certain embodiments, the method further comprises joining the at least one decellularized muscle matrix to at least one decellularized dermal matrix. In some embodiments, the method further comprises blending, cutting, homogenizing, or cryofracturing the muscle implant to form a particulate muscle implant. In some embodiments, the muscle implant is exposed to e-beam radiation.

In various embodiments, a muscle implant is provided, comprising at least one decellularized muscle matrix containing at least some of the myofibers normally found in a muscle tissue prior to processing. In some embodiments, the decellularized muscle matrix contains 20-80% of the myofibers normally found in a muscle tissue prior to processing. In some embodiments, the muscle implant further comprises at least one decellularized dermal matrix joined to the at least one decellularized muscle matrix. In certain embodiments, the muscle implant is in particulate form. In certain embodiments, the muscle implant is lyophilized or provided in aqueous solution.

In various embodiments, a method of treatment is provided, comprising implanting into a patient one of the muscle implants described above. In some embodiments, the muscle implant promotes an increased rate and/or overall amount of native muscle regeneration after implantation into a patient, as compared to the rate and/or overall amount of regeneration in the absence of an implant or in the presence of an implant comprising intact muscle or comprising decellularized muscle that lacks substantially all myofibers. In certain embodiments, the muscle implant is used to treat a skeletal muscle defect such as an abdominal hernia, gunshot wound, or blunt force trauma. In some embodiments, the muscle implant is used after the loss of bulk muscle, for example, due to a muscle wasting disorder or due to the surgical removal of native muscle tissue from a patient (e.g., from a treatment of a sarcoma or osteosarcoma). In certain embodiments, the muscle implant is used to enhance the appearance and/or volume of muscle tissue at an implant site

DESCRIPTION OF CERTAIN EXEMPLARY EMBODIMENTS

Figure 1:
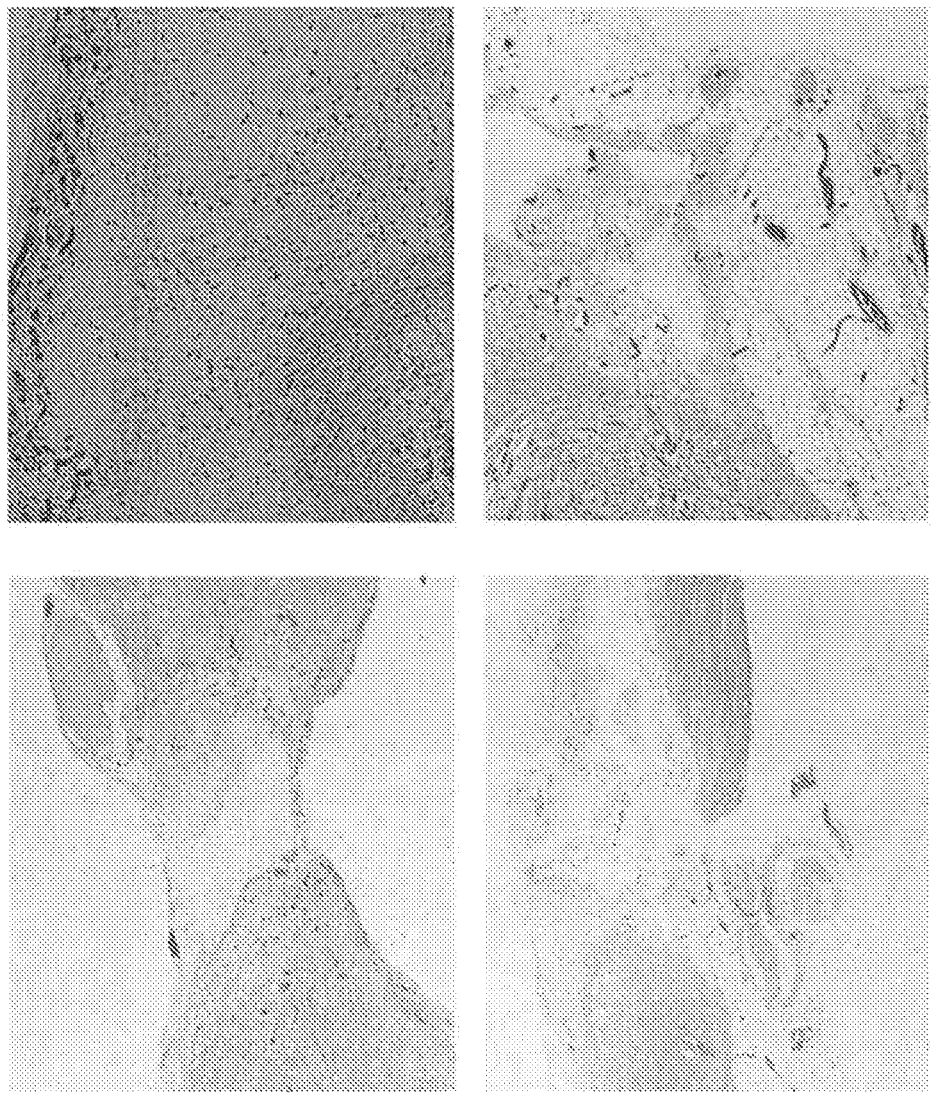
FIG. 1 shows H&E (left column) and trichrome (right column) staining of sections of a 1 $cm^2$ defect in rat gluteus maximus muscle that was left untreated. Sections were taken 3 weeks (upper row) and 6 weeks (lower row) after defect creation.

Reference will now be made in detail to certain exemplary embodiments according to the present disclosure, certain examples of which are illustrated in the accompanying drawings.

Disclosed herein are muscle implants comprising one or more decellularized muscle matrices. In some embodiments, the decellularized muscle matrices are prepared by selecting a suitable sample of muscle tissue, washing the sample to remove red blood cells and other debris, exposing the muscle sample to trypsin, exposing the muscle sample to a decellularization solution, optionally contacting the decellularized muscle sample with DNase and/or alpha-galactosidase, washing the decellularized muscle sample a second time, and, optionally, sterilizing the sample. In certain embodiments, the extent of myofiber removal from the muscle sample is controlled by altering the concentration and/or the length of time in which the muscle sample is exposed to trypsin and/or to the decellularization solution. In some embodiments, the resulting decellularized muscle matrix retains at least some myofibers, e.g., about 20-80% of the myofibers found in a muscle sample prior to processing (decellularization and trypsin treatment).

In various embodiments, the retention of at least some myofibers in the muscle matrix can result in an increased rate and/or overall amount of native muscle repair and/or regeneration after implantation in a patient having a muscle defect in need of repair. In some embodiments, the retention of at least some myofibers in the muscle matrix induces a level of inflammation sufficient to recruit the native muscle repair machinery, thereby enhancing the kinetics and/or extent of native muscle repair. In contrast, a muscle defect that does not receive an implant or receives an implant comprising a decellularized tissue that lacks any retained myofibers may not induce sufficient inflammation to substantially recruit the native muscle repair machinery. This may result in slower muscle regeneration kinetics and a predominance of fibroblast rather than myoblast infiltration at the implant site. Likewise, an implant comprising intact muscle (i.e., muscle that has not been decellularized) may cause excess inflammation, resulting in increased scar tissue formation and a lack of myoblast infiltration.

In various embodiments, a muscle implant comprising a particulate decellularized muscle matrix is disclosed. For example, the decellularized muscle matrices described above can be cut, blended, cryofractured, or otherwise homogenized to form particulate matrices that can be lyophilized and stored dry, or stored suspended in a gel, hydrogel, or other aqueous solution. In some embodiments, a particulate decellularized muscle matrix can be used as a flowable and/or injectable composition that can be readily molded to fill an implant site and used to repair a muscle defect.

In some embodiments, a decellularized muscle matrix can be joined to a decellularized dermal matrix to form a bilayer implant. In some embodiments, the dermal matrix can provide initial structural strength and/or load bearing capacity, and can also enhance the repair or treatment of a muscle defect by allowing for improved regeneration of both the muscle and the underlying fascia tissue layers. In certain embodiments, the decellularized dermal matrix can improve the ability of the bilayer implant to tolerate torsional or other forces experienced after implantation, thereby stabilizing the implant during the migration and proliferation of myocytes into the scaffold provided by the muscle matrix. In some embodiments, the load bearing capacity of a bilayer implant is transferred over time following implantation from the dermal portion of the implant to the muscle portion, which is initially weaker, as muscle regeneration progresses and strengthens the muscle tissue, and as the implanted dermal tissue degrades. In various embodiments, the muscle matrix and dermal matrix can be secured to each other using biocompatible glues, sutures, and/or any other known means of securing biological materials.

The muscle implants of the present disclosure can be used to treat various muscle defects and related disorders. For example, the implants can be used to treat hernias and other abdominal wall muscle injuries, where the current standard of care generally involves the use of fully decellularized dermal matrices and intact muscle transplants that are more effective in promoting fascia regeneration rather than the regeneration of the overlying muscle. In another example, the implants can be used to repair a traumatic abdominal wall injury, such as from a gunshot or other blunt force injury. In yet another example, the implants can be used following the surgical removal of bulk tissue (e.g., after removal of a soft tissue sarcoma or osteosarcoma).

As used herein, "myofibers" are the rod-like structures involved in muscle contraction and comprise proteins such as myosin, troponin, tropomyosin, and actinin. Long myofiber chains are found in and between the elongated muscle cells (myocytes).

As used herein, a "muscle defect" is any muscle abnormality or damage that is amenable to repair, improvement, enhancement, regeneration, amelioration, and/or treatment by an implanted muscle matrix. A muscle defect encompasses any abnormality or damage resulting from disease, trauma, or surgical intervention that results in an alteration to the muscle. As used herein, the removal or loss of "bulk" muscle tissue refers to the loss of an appreciable and measurable volume of muscle tissue, e.g., a volume of at least about 0.5 $cm^3$.

As used herein, a "decellularized tissue" is any tissue from which most or all of the cells that are normally found growing in the extracellular matrix of the tissue have been removed (e.g., a tissue lacking about 80, 85, 90, 95, 99, 99.5, or 100% of the native cells) (or any percentage in between).

The materials and methods provided herein can be used to make a biocompatible implant. As used herein, a "biocompatible" implant is a composition that has the ability to support the migration and proliferation of native cells from surrounding tissue into the composition following implantation and does not elicit a substantial immune response that prevents such cellular activity. As used herein, a "substantial immune response" is one that prevents partial or complete resorption of the implanted material and/or the partial or complete repopulation of the implant with native cells.

As used herein, the terms "native cells" and "native tissue" mean the cells and tissue present in the recipient tissue/organ prior to the implantation of a muscle implant, or the cells or tissue produced by the host animal after implantation.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. To the extent publications and patents or patent applications incorporated by reference contradict the invention contained in the specification, the specification will supersede any contradictory material.

In this application, the use of the singular includes the plural unless specifically stated otherwise. Also in this application, the use of "or" means "and/or" unless stated otherwise. Furthermore, the use of the term "including," as well as other forms, such as "includes" and "included," are not limiting. Any range described here will be understood to include the endpoints and all values between the endpoints.

Muscle Implants

Disclosed herein are muscle implants. In various embodiments, a muscle implant can comprise one or more muscle matrix derived from human or animal muscle tissue that has been decellularized but retains at least some myofibers.

A muscle matrix can be derived from any human or animal muscle tissue that is suitable for decellularization and subsequent implantation. In certain embodiments, the muscle is a skeletal muscle. A muscle matrix can comprise muscle tissue from one or more (e.g., 1, 2, 3, 4, 5, or more) different muscles. In certain embodiments, the muscle can come from human or non-human sources. Exemplary non-human sources include, but are not limited to, pigs, sheep, goats, cows, rabbits, monkeys, and/or other non-human mammals. A muscle matrix can comprise muscle from one or more (e.g., 1, 2, 3, 4, 5, or more) different animal sources.

In various embodiments, the extracellular scaffold within a decellularized muscle tissue may consist of collagen (particularly collagen type I or type III), elastin, myofiber, and/or other fibers, as well as proteoglycans, polysaccharides and/or growth factors (e.g., IGF, EGF, Ang 2, HGF, FGF, and/or VEGF). The muscle matrix may retain some or all of the extracellular matrix components that are found naturally in a muscle prior to decellularization, or various undesirable components may be removed by chemical, enzymatic and/or genetic means. In general, the muscle extracellular matrix provides a structural scaffold comprising fibers, proteoglycans, polysaccharides, and growth factors into which native cells and vasculature can migrate, grow, and proliferate after implantation in a patient. The exact structural components of the extracellular matrix will depend on the type of muscle selected and the processes used to prepare the decellularized tissue.

In some embodiments, a muscle matrix lacks certain undesirable antigens. For example, certain animal tissues contain alpha-galactose (α-gal) epitopes that are known to elicit reactions in humans. Therefore, muscle matrices derived from these animal tissues can be produced or processed to lack certain antigens, such as α-gal. In some embodiments, muscle matrices lack substantially all α-gal moieties. Elimination of the α-gal epitopes may diminish the immune response against the muscle matrix. U. Galili at al., *J. Biol. Chem.* 263: 17755 (1988). Since non-primate mammals (e.g., pigs) produce α-gal epitopes, xenotransplantation of decellularized muscle from these mammals into primates may result, in some instances, in rejection because of primate anti-gal binding to the α-gal epitopes on the muscle matrix. U. Galili et al., *Immunology Today* 14: 480 (1993); M. Sandrin et al., *Proc. Natl. Acad. Sci. USA* 90: 11391 (1993); H. Good at al., *Transplant. Proc.* 24: 559 (1992); B. H. Collins et al., *J. Immunol.* 154: 5500 (1995).

As described in detail below, in various embodiments, muscle matrices can be processed to remove antigens such as α-gal, e.g., by chemical or enzymatic treatment. Alternatively, in some embodiments, muscle matrices can be produced from animals that have been genetically modified to lack these epitopes.

In certain embodiments, a muscle implant can comprise one or more additional agents. In some embodiments, the additional agent(s) can comprise an anti-inflammatory agent, an analgesic, or any other desired therapeutic or beneficial agent. In certain embodiments, the additional agent(s) can comprise, e.g., at least one added growth or signaling factor (e.g., a cell growth factor, an angiogenic factor, a differentiation factor, a cytokine, a hormone, and/or a chemokine). These additional agents can promote native muscle migration, proliferation, and/or vascularization. In some embodiments, the growth or signaling factor is encoded by a nucleic acid sequence contained within an expression vector. As used herein, the term "expression vector" refers to any nucleic acid construct that is capable of being taken up by a cell, contains a nucleic acid sequence encoding a desired protein, and contains the other necessary nucleic acid sequences (e.g. promoters, enhancers, initiation and termination codons, etc.) to ensure at least minimal expression of the desired protein by the cell.

In various embodiments, the decellularized muscle matrix in a muscle implant retains at least some of the myofibers found in the muscle tissue prior to processing. In some embodiments, the muscle matrix retains about 20-80% of the myofibers found in the muscle tissue prior to processing (e.g., about 20, 30, 40, 50, 60, 70, or 80%) (or any percentage in between).

The muscle implants disclosed herein can be in either particulate or non-particulate form. When in non-particulate form, the implant can be in any desirable shape, e.g., a sheet, cube, sphere, or other desired shape. In some embodiments, a non-particulate muscle implant can have a thickness of up to about 20 mm (e.g., about 5, 10, 15, or 20 mm thick, or any thickness in between). Particulate implants (e.g., implants that have been cut, blended, cryofractured, or otherwise homogenized) can be stored dry (e.g., lyophilized) or suspended in a gel (e.g., gelatin), hydrogel, or other aqueous solution (e.g., phosphate buffered saline or any other biocompatible saline solution).

In various embodiments, a muscle implant can comprise a decellularized muscle matrix joined to a decellularized dermal matrix to form a bilayer implant. In some embodiments, the decellularized dermal matrix can comprise ALLODERM® or STRATTICE™ (LIFECELL Corporation, Branchburg, N.J.), which are decellularized human and porcine dermal matrices, respectively. Alternatively, any other suitable decellularized dermal matrices can be used. In various embodiments, the muscle matrix and dermal matrix can be secured to each other using any known means of securing biological materials. For example, the muscle matrix and dermal matrix can be secured using biocompatible sutures and/or staples. In another example, a biocompatible glue (e.g., fibrin glue) can be used to secure the two matrix layers. In yet another example, the muscle matrix and dermal matrix can be mechanically joined by applying pressure to the two layers and/or by exposing the bilayer implant to one or more crosslinking methods (e.g., a chemical crosslinking agent, dehydrothermal treatment, and/or irradiation, including E-beam irradiation).

In various embodiments, a muscle implant as disclosed herein can comprise one or more decellularized muscle matrix (e.g., 1, 2, 3, 4, 5, or more) and/or one or more decellularized dermal matrix (e.g., 1, 2, 3, 4, 5, or more). Where more than one muscle matrix and/or dermal matrix is used, these can be secured to each using any of the means discussed above for securing the bilayer implants.

In various embodiments, a muscle implant can comprise a decellularized tissue that is harvested from the transition region between a muscle and a tendon. For example, a muscle implant can comprise a decellularized tissue from the transition region between an extensor muscle and proximal tendon. In some embodiments, the muscle portion of the decellularized transition region tissue retains at least some (e.g., about 20-80%) of the myofibers found in the muscle tissue prior to processing. In some embodiments, the tendon portion of the decellularized transition region tissue retains some or all of the collagen fibrils found in the tendon tissue prior to processing. In various embodiments, the tendon portion of the decellularized transition region tissue provides increased tensile and/or torsional strength to the muscle implant, as compared to a muscle implant that does not comprise decellularized tendon tissue.

Muscle implants, as described above, may be packaged and/or stored as frozen, freeze-dried, hydrated, and/or dehydrated products. In certain embodiments, the packaged muscle implants have reduced bioburden or are sterile. In certain embodiments, a kit is provided, comprising one or more packaged muscle implant(s) and instructions for preparing and/or using the implant(s).

Methods of Making Muscle Implants

Disclosed herein are methods of making muscle implants. In various embodiments, a muscle implant comprises one or more decellularized muscle matrices that are prepared by selecting suitable muscle samples, washing the samples to remove red blood cells and other debris, exposing the muscle samples to trypsin, exposing the muscle samples to a decellularization solution, optionally contacting the decellularized muscle samples with DNase and/or alpha-galactosidase, washing the decellularized muscle samples, and, optionally, sterilizing the samples. In certain embodiments, the extent of myofiber removal from the muscle sample is controlled by altering the concentration and/or length of time in which the muscle sample is exposed to trypsin and/or to the decellularization solution. In some embodiments, the resulting muscle matrix retains at least some myofibers.

In some embodiments, a muscle matrix can be prepared from a sample of any muscle tissue that is suitable for decellularization and subsequent implantation. In certain embodiments, the muscle sample can be from a mammalian muscle tissue, such as a mammalian skeletal muscle. In some embodiments, the muscle sample used to prepare a muscle matrix can encompass the transition region between a muscle and a tendon (e.g., the transition region between an extensor muscle and tendon), thereby providing a muscle sample having both muscle and tendon tissue in it. In some embodiments, the muscle matrix can comprise human and/or non-human sources. Exemplary, suitable non-human muscle tissue sources include, but are not limited to, pigs, sheep, goats, cows, rabbits, monkeys, and/or other non-human mammals.

In some embodiments, a muscle matrix is prepared by decellularizing a muscle sample while retaining at least some myofibers. In some embodiments, the decellularized muscle matrix provides a porous extracellular scaffold structure into which myocytes from surrounding native tissue can migrate and proliferate after implantation in a host site. In certain embodiments, the decellularized muscle matrix activates the patient's inflammatory and/or muscle repair mechanisms.

In various embodiments, the general steps involved in the production of a decellularized muscle matrix include providing a sample of muscle tissue or transition region tissue from a donor (e.g., a human cadaver or animal tissue source) and removing cellular material under conditions that preserve some or all of the biological and/or structural functions of the extracellular matrix in the sample, as well as at least some of the myofibers.

In some embodiments, a sample of muscle tissue can be provided and washed to remove any residual cryoprotectants, red blood cells, and/or any other contaminants. Solutions used for washing can be any physiologically-compatible solution. Examples of suitable wash solutions include distilled water, phosphate buffered saline (PBS), or any other biocompatible saline solution.

In certain embodiments, the sample of muscle tissue can be chemically treated to stabilize the tissue so as to avoid biochemical and/or structural degradation before, during, or after cell removal. In various embodiments, the stabilizing solution arrests and prevents osmotic, hypoxic, autolytic, and/or proteolytic degradation; protects against microbial contamination; and/or reduces mechanical damage that can occur during decellularization. The stabilizing solution may contain an appropriate buffer, one or more antioxidants, one or more oncotic agents, one or more antibiotics, one or more protease inhibitors, and/or one or more smooth muscle relaxants.

In various embodiments, the sample of muscle tissue can be exposed to trypsin in order to break down muscle fiber bundles (e.g., by cleaving myosin molecules in the muscle fiber). In some embodiments, trypsin can facilitate the decellularization process by increasing the rate and/or extent of myofiber breakdown and myocyte removal during subsequent decellularization. In some embodiments, the muscle sample is exposed to trypsin at a concentration of about 0.02-0.5% (e.g., at about 0.02, 0.03, 0.04, 0.05, 0.06, 0.07, 0.08, 0.09, 0.1, 0.15, 0.2, 0.25, 0.3, 0.35, 0.4, 0.45, or 0.5%) (or any percentage in between). In certain embodiments, the muscle sample is exposed to trypsin for at least about 15 minutes and/or up to a maximum of about 120 minutes (e.g., about 15, 30, 45, 60, 75, 90, 105, or 120 minutes) (or any time period in between). The length of time of trypsin exposure, and/or the concentration of trypsin, can be adjusted in order to control the extent of myofiber removal from the muscle tissue so as to retain at least some of the myofibers in the muscle matrix after trypsinization and decellularization. In some embodiments, the trypsinized tissue is then neutralized, for example using fetal bovine serum (e.g., at a concentration of 1-5%) in phosphate buffered saline, optionally with the addition of gentamycin (e.g., at a concentration of 0.1-3%). In some embodiments, the neutralization reaction is allowed to proceed for at least about 1 hour (e.g., at least about 1, 2, 3, 4, or 5 hours) (or any time period in between).

In various embodiments, the sample of muscle tissue can be placed in a decellularization solution in order to remove viable and non-viable cells from the muscle tissue without damaging the biological and/or structural integrity of the extracellular matrix. The decellularization solution may contain an appropriate buffer, salt, an antibiotic, one or more detergents (e.g., TRITON X-100™, sodium dodecyl sulfate, sodium deoxycholate, polyoxyethylene (20) sorbitan monolaurate, etc.), one or more agents to prevent cross-linking, one or more protease inhibitors, and/or one or more enzymes. In some embodiments, the decellularization solution comprises 0.1%, 0.2%, 0.3%, 0.4%, 0.5%, 1.0%, 1.5%, 2.0%, 2.5%, 3.0%, 3.5%, 4.0%, 4.5%, or 5.0% (or any percentage in between) of TRITON X-100™ and, optionally, 10 mM, 15 mM, 20 mM, 25 mM, 30 mM, 35 mM, 40 mM, 45 mM, or 50 mM EDTA (ethylenediaminetetraacetic acid) (or any concentration in between). In certain embodiments, the decellularization solution comprises 0.1%, 0.2%, 0.3%, 0.4%, 0.5%, 1.0%, 1.5%, 2.0%, 2.5%, 3.0%, 3.5%, 4.0% 4.5%, or 5.0% (or any percentage in between) of sodium deoxycholate and, optionally, 1 mM, 2 mM, 3 mM, 4 mM, 5 mM, 6 mM, 7 mM, 8 mM, 9 mM, 10 mM, 11 mM, 12 mM, 13 mM, 14 mM, 15 r M, or 20 mM HEPES buffer (4-(2-hydroxyethyl)-1-piperazneethanesulfonic acid) containing 10 mM, 15 mM, 20 mM, 25 mM, 30 mM, 35 mM, 40 mM, 45 mM, or 50 mM EDTA (or any concentrations in between). In some embodiments, the muscle tissue is incubated in the decellularization solution at 20, 21, 22, 23, 24, 25, 30, 31, 32, 33, 34, 35, 36, 37, 38, 39, 40, 41, or 42 degrees Celsius (or any temperature in between), and optionally, gentle shaking is applied at 10, 20, 30, 40, 50, 60, 70, 80, 90, 100, 110, 120, 130, 140, or 150 rpm (or any rpm in between). The incubation can be for 1, 2, 3, 4, 5, 6, 7, 8, 9, 10, 11, 12, 15, 20, 24, 36, 48, 60, 72, 84, or 96 hours (or any time period in between). The length of time of exposure to the decellularization solution, and/or the concentration of detergent or other decellularizing agents, can be adjusted in order to control the extent of decellularization and myofiber removal from the muscle tissue. In certain embodiments, additional detergents may be used to remove cells from the muscle tissue. For example, in some embodiments, sodium deoxycholate and TRITON X-100™ can be used to decellularize and separate undesired tissue components from the extracellular tissue matrix. Decellularization can be done after trypsinization, or vice versa.

In various embodiments, the length of exposure and/or the concentration of the decellularization solution and/or trypsin solution can be adjusted in order to control the extent of myofiber removal. In some embodiments, the duration and/or concentration are selected in order to remove about 20-80% of the myofibers normally found in the muscle sample prior to trypsinization and decellularization. In certain embodiments, the duration and/or concentration are selected in order to remove about 20, 30, 40, 50, 60, 70, or 80% of the myofibers (or any percentage in between). In some embodiments, about 20-80% of the myofibers are removed by exposing the muscle tissue sample to trypsin at a concentration ranging from 0.01-0.5% for 15-120 minutes and/or by exposing the muscle tissue sample to about 0.1-2.0% of a decellularization agent (e.g., TRITON X-100™, sodium dodecyl sulfate, sodium deoxycholate, polyoxyethylene (20) sorbitan monolaurate, etc.) for 1-72 hours.

In various embodiments, about 20-80% of the myofibers normally found in a muscle sample are removed by controlling the tissue to volume ratio (e.g., the mass of tissue per volume of solution containing trypsin and/or decellularizing agents). In some embodiments, a lower tissue/volume ratio increases the efficiency of the myofiber removal process, thus resulting in a muscle matrix that retains fewer intact myofibers. In other embodiments, a higher tissue/volume ratio reduces the efficiency of the myofiber removal process, thus resulting in a muscle matrix that retains more intact myofibers.

In some embodiments, after decellularization, the muscle tissue is washed thoroughly. Any physiologically compatible solutions can be used for washing. Examples of suitable wash solutions include distilled water, phosphate buffered saline (PBS), or any other biocompatible saline solution. In some embodiments, the wash solution can contain a disinfectant. In certain embodiments, the disinfectant is peracetic acid (PAA), for example at a concentration of 0.05, 0.1, 0.15, 0.2, 0.25, 0.3, 0.4, or 0.5% (or any percentage in between). In certain embodiments, e.g., when xenogenic or allogenic material is used, the decellularized muscle tissue is treated (e.g., overnight at room temperature) with a deoxyribonuclease (DNase) solution. In some embodiments, the tissue sample is treated with a DNase solution prepared in a DNase buffer (e.g., 20 mM HEPES (4-(2-hydroxyethyl)-1-piperazineethanesulfonic acid), 20 mM $CaCl_2$ and 20 mM $MgCl_2$). Optionally, an antibiotic solution (e.g., Gentamicin) may be added to the DNase solution. Any suitable DNase buffer and/or antibiotics can be used, as long as the buffer and/or antibiotic provides for suitable DNase activity.

While the decellularized muscle tissue in a muscle implant may be derived from one or more donor animals of the same species as the intended recipient animal, this is not necessarily the case. Thus, for example, the decellularized muscle tissue may be prepared from porcine tissue and implanted in a human patient. Species that can serve as donors and/or recipients of decellularized muscle tissue include, without limitation, mammals, such as humans, nonhuman primates (e.g., monkeys, baboons, or chimpanzees), pigs, cows, horses, goats, sheep, dogs, cats, rabbits, guinea pigs, gerbils, hamsters, rats, or mice. In some embodiments, muscle tissue from more than one donor animal can be used.

In certain embodiments, the muscle tissue used to prepare a muscle matrix can be treated with one or more enzymes to remove undesirable antigens, e.g., an antigen not normally expressed by the recipient animal and thus likely to lead to an immune response and/or rejection of a muscle implant comprising the muscle matrix. For example, in certain embodiments, muscle tissue can be treated with alpha-galactosidase to remove alpha-galactose (α-gal) moieties. In some embodiments, to enzymatically remove α-gal epitopes, after washing the muscle tissue thoroughly with saline, the tissue may be subjected to one or more enzymatic treatments to remove α-gal antigens, if present in the sample. In certain embodiments, the muscle tissue may be treated with an α-galactosidase enzyme to substantially eliminate α-gal epitopes. In one embodiment, the tissue is treated with α-galactosidase at a concentration of about 0.2 U/ml prepared in 100 mM phosphate buffered saline at pH 6.0. In other embodiments, the concentration of α-galactosidase is reduced to about 0.1 U/ml or increased to about 0.3, 0.4, or 0.5 U/ml (or any value in between). In other embodiments, any suitable enzyme concentration and buffer can be used, as long as sufficient antigen removal is achieved. In addition, certain exemplary methods of processing tissues to reduce or remove alpha-1,3-galactose moieties are described in Xu et al., *Tissue Engineering*, Vol, 15, 1-13 (2009), which is hereby incorporated by reference in its entirety.

In certain embodiments, animals that have been genetically modified to lack one or more antigenic epitopes may be selected as the tissue source for a muscle matrix. For example, animals (e.g., pigs) that have been genetically engineered to lack expression of the terminal α-galactose moiety can be selected as the tissue source. For descriptions of appropriate animals and methods of producing transgenic animals for xenotransplantation, see U.S. patent application Ser. No. 10/896,594 and U.S. Pat. No. 6,166,288, which are hereby incorporated by reference in their entirety.

In some embodiments, a muscle implant can be treated to reduce bioburden (i.e. to reduce the number of microorganisms growing on the implant). In some embodiments, the treated implant lacks substantially all bioburden (i.e., the implant is aseptic or sterile). Suitable bioburden reduction methods are known to one of skill in the art, and may include exposing the muscle implant to a compound such as peracetic acid (PAA) or to radiation. Irradiation may reduce or substantially eliminate bioburden. In some embodiments, an absorbed dose of about 14-18 kGy of e-beam radiation is delivered in order to reduce or substantially eliminate bioburden. In various embodiments, a muscle implant is exposed to between about 5 Gy and 50 kGy of radiation (e.g., about 5, 10, 15, 20, 25, 30, 35, 40, 45, or 50 kGy, or any value in between). Suitable forms of radiation can include gamma radiation, e-beam radiation, and X-ray radiation. Other irradiation methods are described in U.S. Application 2010/0272782, the disclosure of which is hereby incorporated by reference in its entirety.

In certain embodiments, one or more additional agents can be added to a muscle implant. In some embodiments, the additional agent can comprise an anti-inflammatory agent, an analgesic, or any other desired therapeutic or beneficial agent. In certain embodiments, the additional agent can comprise at least one added growth or signaling factor (e.g., a cell growth factor, an angiogenic factor, a differentiation factor, a cytokine, a hormone, and/or a chemokine). In some embodiments, these additional agents can promote native myocyte migration, proliferation, and/or vascularization in the extracellular matrix of a muscle implant. In some embodiments, the growth or signaling factor is encoded by a nucleic acid sequence contained within an expression vector. As used herein, the term "expression vector" refers to any nucleic acid construct that is capable of being taken up by a cell, contains a nucleic acid sequence encoding a desired protein, and contains the other necessary nucleic acid sequences (e.g. promoters, enhancers, termination codon, etc.) to ensure at least minimal expression of the desired protein by the cell.

In various embodiments, a muscle implant is prepared by joining a decellularized muscle matrix to a decellularized dermal matrix to form a bilayer implant. In some embodiments, the decellularized dermal matrix is prepared by decellularizing a dermal tissue sample while retaining at least some of the extracellular components (e.g., the collagen scaffold) in the dermal tissue. Exemplary methods for decellularizing dermal tissue and preparing decellularized dermal tissue matrices are disclosed in U.S. Pat. No. 6,933,326 and U.S. Patent Application 2010/0272782, which are hereby incorporated by reference in their entirety. In certain exemplary embodiments, a decellularized dermal matrix comprises ALLODERM® or STRATTICE™ (LifeCell Corporation, Branchburg, N.J.), which are decellularized human dermal products and porcine dermal products, respectively. Alternatively, any other suitable decellularized dermal matrices can be used.

In various embodiments, the decellularized muscle and dermal matrices in a bilayer implant are secured to each other using any known means of securing biological materials. For example, the muscle matrix and dermal matrix can be secured using biocompatible sutures and/or staples. In another example, biocompatible glues (e.g., fibrin glue) are used to secure the two matrix layers. In yet another example, the muscle matrix and dermal matrix can be mechanically joined by applying pressure to the two layers and/or by exposing the bilayer implant to one or more crosslinking methods (e.g., a chemical crosslinking agent, dehydrothermal treatment, and/or irradiation, including E-beam irradiation).

In various embodiments, a muscle implant is prepared, comprising one or more decellularized muscle matrix (e.g., 1, 2, 3, 4, 5, or more) and/or one or more decellularized dermal matrix (e.g., 1, 2, 3, 4, 5, or more). Where more than one muscle matrix and/or dermal matrix is used, these can be secured to each using any of the means discussed above for securing bilayer implants.

In various embodiments, a muscle implant can be provided in particulate form. For example, a muscle implant comprising one or more decellularized muscle matrix and/or one or more decellularized dermal matrix can be cut, blended, homogenized, lyophilized and/or cryofractured. The particulate muscle implant can be stored dry (e.g., lyophilized) or in an aqueous solution. In some embodiments, a particulate muscle implant is provided pre-loaded in a syringe for ease of surgical delivery to an implant site.

Methods of Use

In various embodiments, a muscle implant comprising a decellularized muscle matrix that retains at least some myofibers can be implanted into a patient (e.g., to fill a region of bulk muscle loss or to cosmetically enhance a muscle tissue). In some embodiments, the remaining myofibers in the muscle matrix can induce an inflammatory response at the implant site. In some embodiments, the inflammatory response is sufficient to initiate and/or enhance the patient's muscle repair machinery without causing excessive inflammation that could result in increased scar tissue formation and/or implant rejection. In some embodiments, the induction of an inflammatory response initiates and/or enhances muscle repair in the patient, e.g., by recruiting macrophages and myoblasts that infiltrate the muscle matrix, and by activating satellite cells that differentiate into muscle within the scaffold provided by the muscle matrix, thereby remodeling the implant into muscle tissue. In various embodiments, activation of the innate muscle repair machinery increases the extent and/or kinetics of muscle repair/regeneration at the implant site. In contrast, muscle repair in the absence of an implant, or when using an implant comprising intact muscle or decellularized tissue lacking any myofibers, results in a slower rate of muscle repair and a lower level of muscle tissue formation (and a concomitant increase in connective and/or scar tissue formation).

In various embodiments, a muscle implant comprising one or more decellularized muscle matrices and one or more decellularized dermal matrices is used. The dermal matrix typically provides a stronger material initially, one that can better resist the tensile, torsional, and other forces the implant experiences, thereby protecting the underlying muscle matrix from damage or deformation during the repair/regeneration process. In some embodiments, the dermal matrix can also provide a scaffold into which native cells (e.g., fibroblasts, etc.) can migrate, allowing for the remodeling of fascia and/or dermis along with the remodeled muscle induced by the muscle matrix.

In various embodiments, a muscle implant comprising decellularized tissue harvested from the transition region between a muscle and a tendon is used. In various embodiments, the tendon portion of the decellularized transition region tissue provides increased tensile and/or torsional strength for the muscle implant, as compared to a muscle implant that does not comprise decellularized tendon tissue. In some embodiments, the increased strength allows the implant to better resist the tensile, torsional, and other forces the implant experiences during the regeneration process. In some embodiments, the decellularized tendon portion of the implant provides a collagen scaffold into which native cells (e.g., fibroblasts, etc.) can migrate, allowing for the remodeling of fascia along with the remodeled muscle induced by the decellularized muscle portion of the implant.

In some embodiments, a particulate muscle implant can be used to fill a void space in a muscle tissue. For example, a particulate muscle implant in aqueous solution can be flowed into an implant site, filling a desired space and/or increasing the bulk of a muscle tissue. In some embodiments, a particulate muscle implant can be used to pack the space around a non-particulate muscle implant in order to more fully fill the implant site.

A muscle implant, as disclosed herein, can be used in any surgical procedure where repair, alteration, regeneration, and/or enhancement of muscle tissue is desired. For example, a muscle implant can be used in the repair of abdominal wall defects (e.g., hernia repair, gunshot injury, or other abdominal trauma). When an implant comprising one or more decellularized muscle matrices and one or more decellularized dermal matrices is used, the muscle matrix in the implant can promote muscle regeneration while the dermal matrix in the implant promotes repair of the underlying fascia. In contrast, current surgical procedures (e.g., the use of sutures and/or implanted decellularized dermal matrices that lack myofibers) result in substantial repair of fascia but minimal repair or regeneration of underlying muscle. The lack of underlying muscle regeneration with the current surgical procedures can lead to an increased rate of bulging, scarring, and other complications.

In some embodiments, a muscle implant can also be used after surgical removal of bulk muscle tissue (e.g., after surgical intervention to remove a sarcoma or osteosarcoma). In these embodiments, the muscle implant can initiate and/or improve the rate and overall volume of muscle repair by inducing a sufficient (but not excessive) level of inflammation that serves to recruit the patient's muscle repair pathways (e.g., macrophage/myoblast recruitment and satellite cell activation). In contrast, the rate and overall volume of muscle repair is reduced in patients that do not receive a muscle implant and in patients that receive an implant comprising intact muscle or decellularized tissue that lacks any remaining myofibers. Similarly, in surgical procedures where muscle tissue is harvested from one muscle for transplantation into another location on the patient, a muscle implant as described above can be placed at the harvest site to help promote the rate and overall extent of muscle repair at the harvest site following the transplant procedure.

In some embodiments, a muscle implant can be used to enhance native muscle volume. For example, a muscle implant can be used as part of a treatment for a muscle wasting disease, thereby enhancing the rate of repair and regeneration, and/or increasing the overall volume of muscle at the implant site. In another example, the implant can be used to cosmetically enhance the appearance of muscle tissue by promoting the growth of additional muscle volume at the implant site.

EXAMPLES

The following examples serve to illustrate, and in no way limit, the present disclosure.

Example 1: Preparation of Muscle Implants

Porcine skeletal muscle was dissected and washed for three days to remove red blood cells. Muscle samples were treated with 0.25% trypsin for 1 hour before being neutralized for 2 hours using 5% fetal bovine serum diluted in PBS and 1% gentamicin. Samples ere then placed in a decellularization solution containing sodium deoxycholate plus 0.2% Triton X-100 overnight, before being washed in HEPES solution for one hour. Samples were treated with DNase overnight to remove any DNA remaining in the tissue, and then treated overnight with alpha-galactosidase to remove alpha gal epitopes on the tissue. Samples were exposed to PAA for 2 hours, washed, and exposed to e-beam radiation.

The extent of myofiber removal was adjusted by controlling the exposure to trypsin and to the decellularization solution.

Analysis of the decellularized muscle indicated insignificant levels of IGF, EGF, Ang 2, and HGF, with trace amounts of VEGF detected. By reducing the processing time, the decellularized muscle matrices retained significant amounts of FGF. An analysis of collagen in the intact and decellularized matrices showed the presence of collagen I and collagen III, with a predominance of collagen I.

Example 2: Repair of Muscle Critical Size Defects

A 1 $cm^2$ critical size defect was made in rat gluteus maximus muscle and evaluated at two time points—3 weeks and 6 weeks post operation. The 1 $cm^2$ defect represents a standard size used in the study of volumetric muscle loss. When left untreated, very little repair occurred in the defect at 3 weeks and 6 weeks, but some myogenesis activity was observed at the ends of the damaged muscle. FIG. 1.

To evaluate the effectiveness of different implants, 5 repair groups were used—defects repaired with Strattice™, defects repaired using decellularized porcine muscle prepared according to the Wake Forest method, defects repaired with intact porcine muscle, defects repaired with decellularized porcine muscle that retained some myofibers (as described in Example 1), and defects repaired with completely decellularized porcine muscle that lacked any retained myofibers. The Wake Forest method for preparing a tissue matrix involves a trypsinization step, followed by trypsin neutralization and 5 days of decellularization in a 1% Triton X-100 solution (without DNase or alpha gal treatment).

Figure 2:
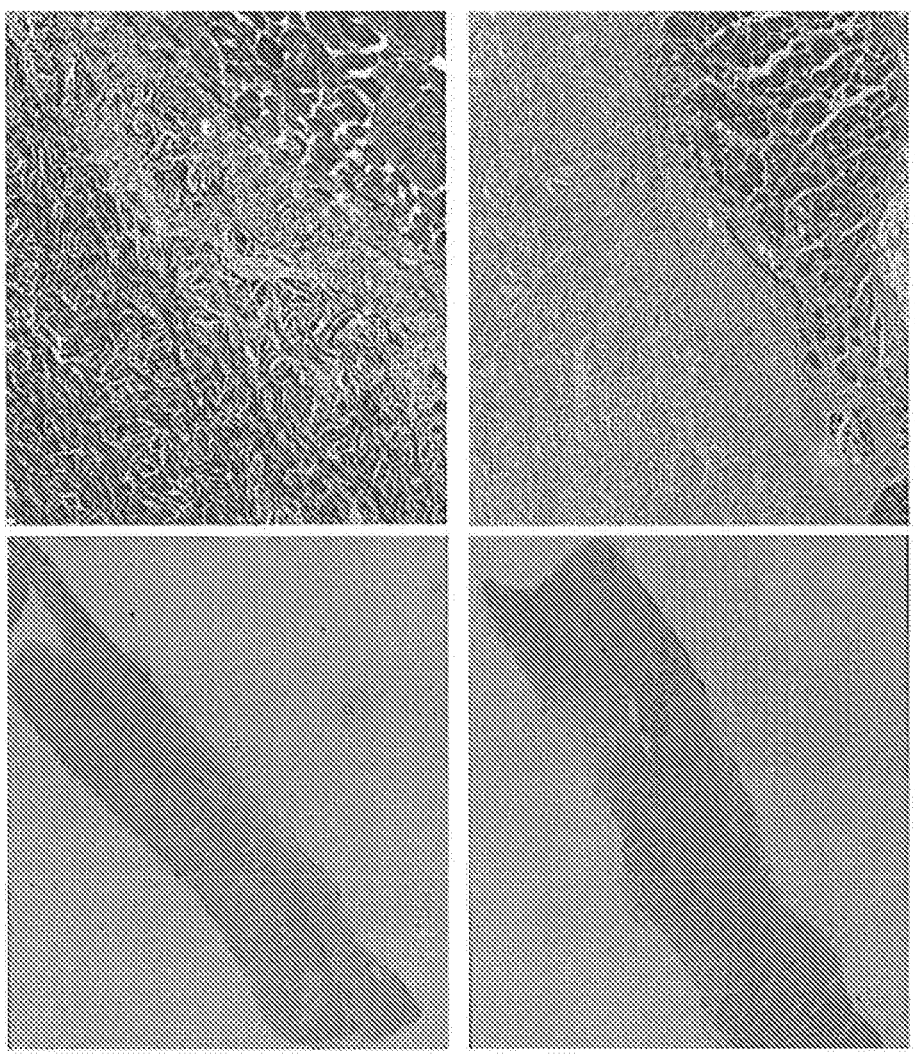
FIG. 2 shows H&E (left column) and trichrome (right column) staining of sections of a 1 $cm^2$ defect in rat gluteus maximus muscle that was repaired with Strattice™. Sections were taken 3 weeks (upper row) and 6 weeks (lower row) after defect creation.

As shown in FIG. 2, the defects repaired using Strattice™ showed no sign of integration into skeletal muscle after 3 or 6 weeks. The implants had some cell infiltration but no signs of myogenesis at 3 or 6 weeks.

Figure 3:
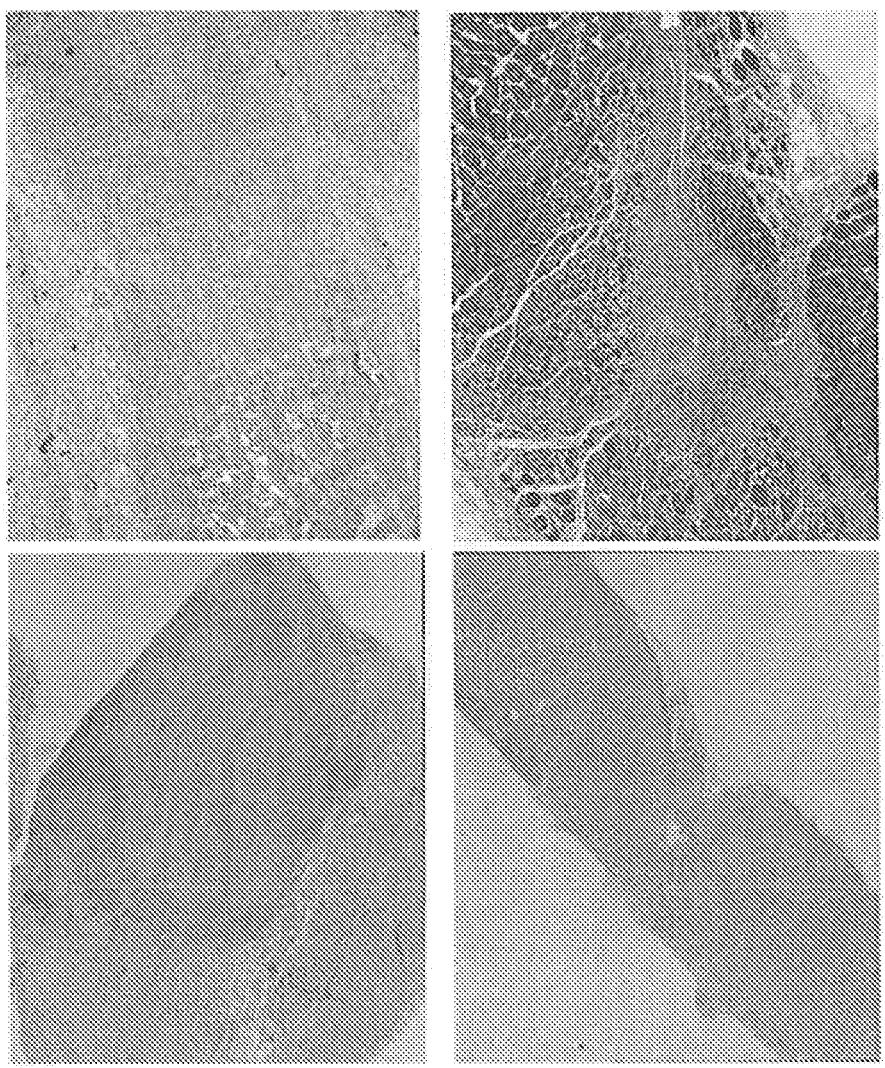
FIG. 3 shows H&E (left column) and trichrome (right column) staining of sections of a 1 $cm^2$ defect in rat gluteus maximus muscle that was repaired with decellularized muscle prepared according to the Wake Forest method. Sections were taken 3 weeks (upper row) and 6 weeks (lower row) after defect creation.

As shown in FIG. 3, the defect repaired using decellularized muscle prepared according to the Wake Forest method induced large scale inflammation throughout the implant after 3 weeks. No fibrous capsule border was detectable after 3 weeks, and the implant was undetectable after 6 weeks. The defect appeared close to fully repaired at 6 weeks.

Figure 4:
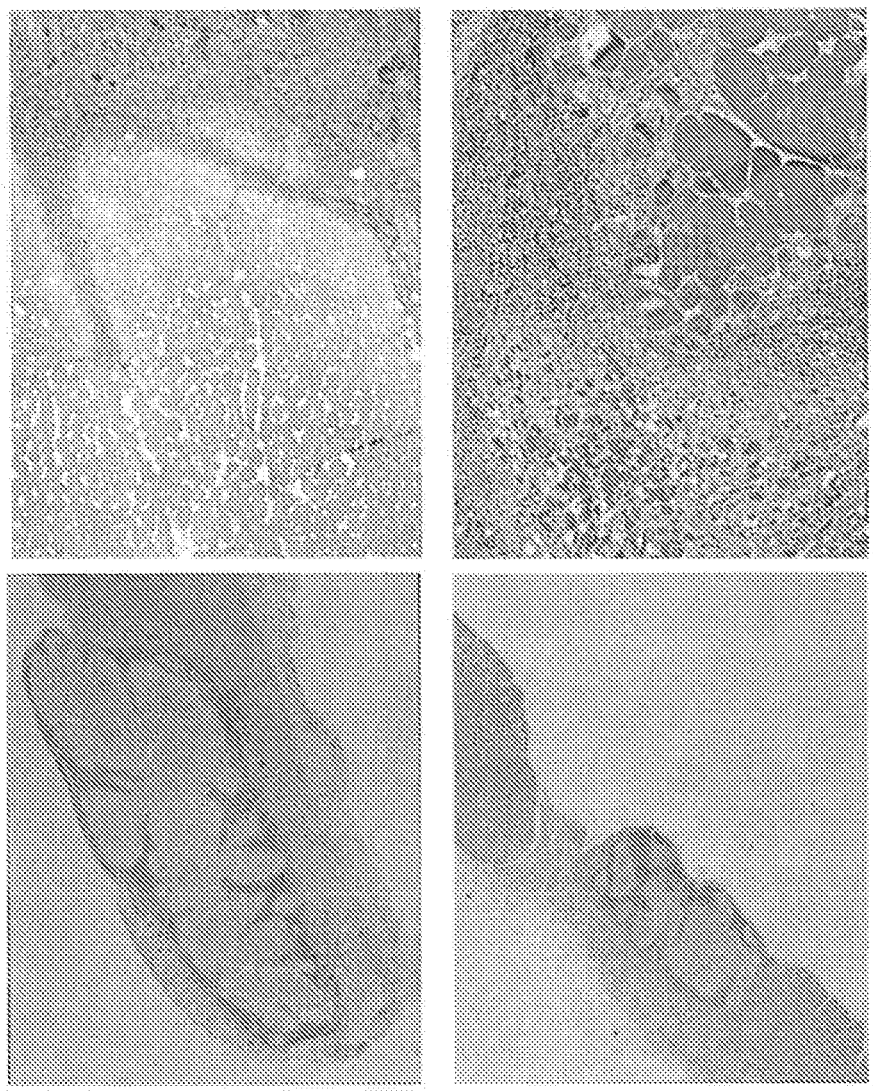
FIG. 4 shows H&E (left column) and trichrome (right column) staining of sections of a 1 $cm^2$ defect in rat gluteus maximus muscle that was repaired with intact muscle. Sections were taken 3 weeks (upper row) and 6 weeks (lower row) after defect creation.

As shown in FIG. 4, when the defect was repaired using intact muscle, the implant was still detectable at 3 weeks and 6 weeks, with significant inflammation around the border of the implant. At least some of the implant remained intact at 6 weeks, with a significant amount of myogenesis around the border of the implant.

Figure 5:
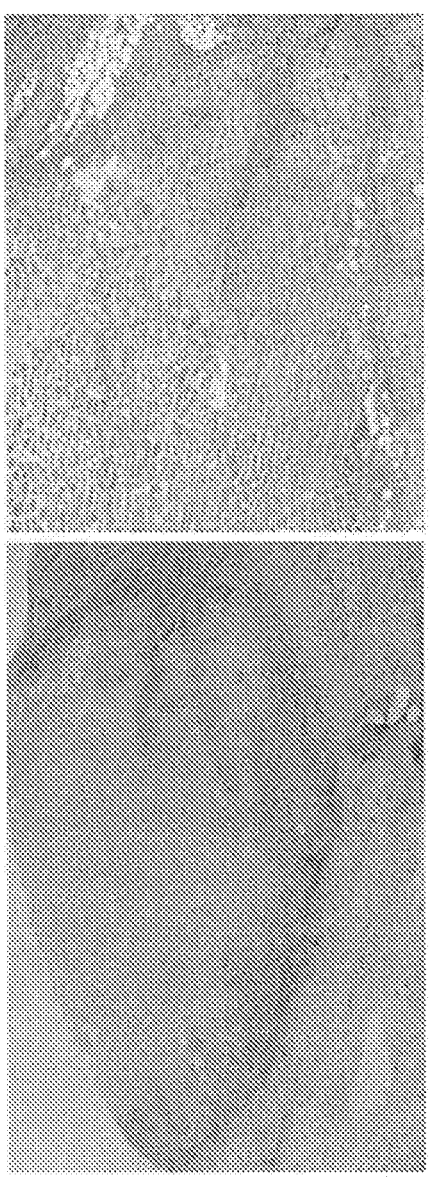
FIG. 5 shows H&E (left column) and trichrome (right column) staining of sections of a 1 $cm^2$ defect in rat gluteus maximus muscle that was repaired with decellularized muscle having some retained myofibers. Sections were taken 3 weeks (upper row) and 6 weeks (lower row) after defect creation.
Figure 5:
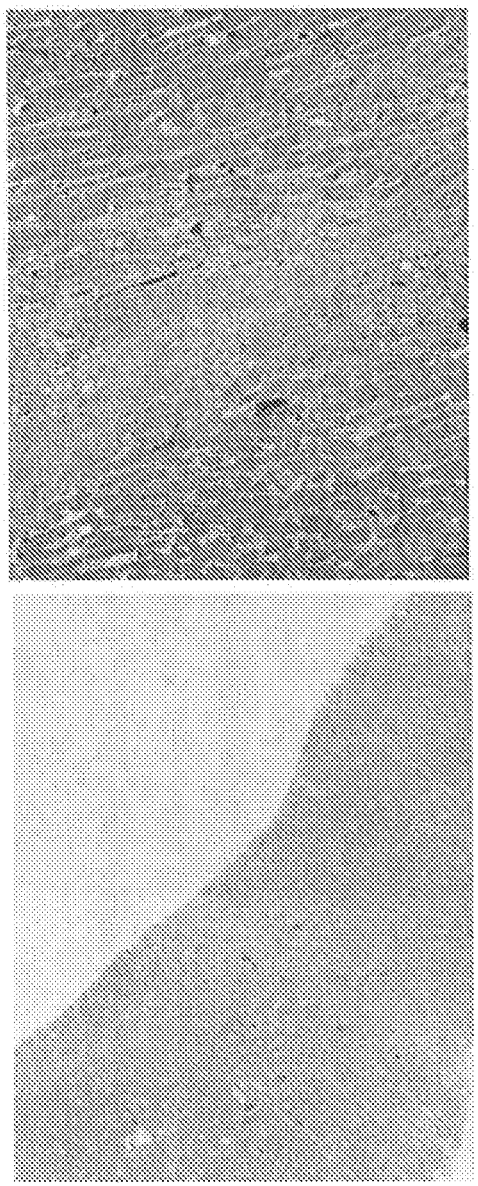

As shown in FIG. 5, when the defect was repaired using decellularized muscle that retained some myofibers, the implant was still noticeable at 3 weeks but not detectable at 6 weeks. The inflammation observed at 3 weeks was at a lower level than that observed for the Wake Forest method. Almost perfect healing of the defect was observed after 6 weeks.

Figure 6:
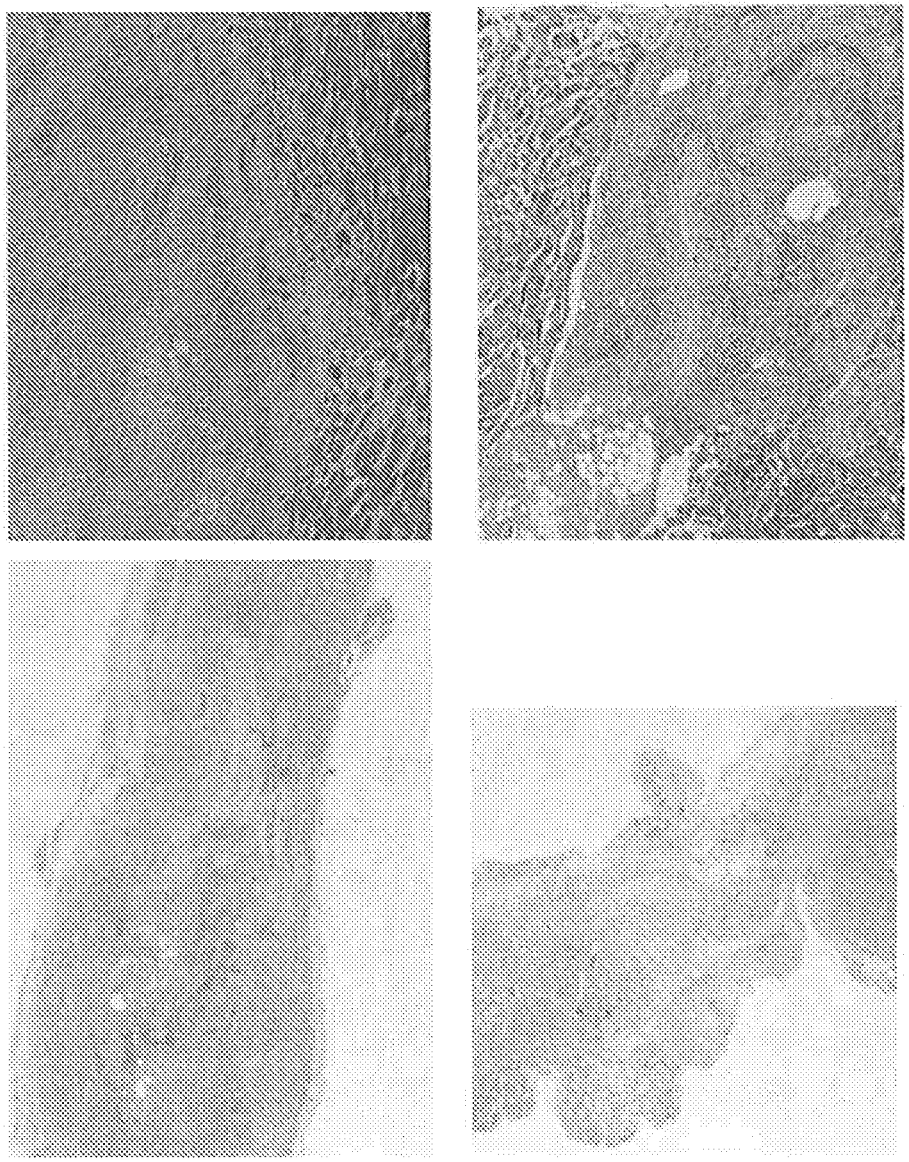
FIG. 6 shows H&E (left column) and trichrome (right column) staining of sections of a 1 $cm^2$ defect in rat gluteus maximus muscle that was repaired with completely decellularized muscle (no myofiber retention). Sections were taken 3 weeks (upper row) and 6 weeks (lower row) after defect creation.

As shown in FIG. 6, when the defect was repaired using completely decellularized porcine muscle that lacked any retained myofibers, the implant was detectable both at 3 weeks and 6 weeks post implantation. Some inflammation was observed at 3 weeks, which was reduced at 6 weeks. The kinetics of muscle regeneration was very slow and was comparable to the kinetics observed when using Strattice™.

To further evaluate the ability of the different implants to induce muscle regeneration, tissue samples were stained for MYH3, an embryonic muscle marker that is transiently upregulated during early myogenesis. MYH3 expression was not observed in Strattice™ implants, some expression was observed in Wake Forest, intact, and completely decellularized implants, and high expression levels were observed for the decellularized implants that retained some myofibers.

Example 3: Injectable Delivery of Decellularized Muscle

An excision wound model (1 cm×1 cm×0.5 cm defect of skeletal muscle) was used to evaluate the muscle regeneration potential of decellularized skeletal muscle in Sprague Dawley rats. This study used 30 rats divided into 4 groups of 6 animals each. In groups 1 and 2, the excised tissue was repaired by filling the defect with decellularized porcine skeletal muscle that retained some or no myofibers, respectively. In group 3, the muscle defect was filled with a paste-like mixture of hyaluronic acid solution (HA, 5% by weight) and a decellularized porcine muscle powder that retained some myofibers (200 mg/mL). In group 4, the muscle defect was filled with a paste-like mixture of Strattice™ powder mixed in HA solution. Groups 3 and 4 were used to evaluate an injectable approach for delivering decellularized muscle implants.

Following implantation, the animals were observed daily for any abnormal clinical signs, with special attention to the potential changes in gaiting patterns of the rats. Three animals from each group were sacrificed at 3 weeks and the remaining three animals were sacrificed at 6 weeks post implantation. Table 1 summarizes the treatment groups and experimental end points.

TABLE 1

| Group | Test material | Treatments | Number of animals | Time point (weeks) |
|---|---|---|---|---|
| 1 | decellularized muscle with retained myofibers | Implanted on the day of defect creation | 8 | 3, 6 |
| 2 | Completely decellularized muscle - no retained myofibers | Implanted on the day of defect creation | 6 | 3, 6 |
| 3 | HA solution + decellularized muscle fragments | Implanted on the day of defect creation | 3 | 3 |
| 4 | HA solution + Strattice ™ fragments | Implanted on the day of defect creation | 3 | 3 |

The impact of treatment on muscle regeneration was assessed by evaluating the extent of muscle repair based on histopathology and immunostaining. The group 1 implant was visible under gross observation at 3 weeks but no longer distinguishable from host muscle tissue at 6 weeks. The size of the muscle graft was also noticeably smaller than the initial graft size. The histology section for the group 1 implant at 3 weeks showed the predicted inflammatory response around the border of the tissue that is typical of muscle repair. No fibrous capsule was observed throughout the study. The histology section at 6 weeks showed excellent muscle repair in which the muscle defect was close to completely healed with host muscle tissue. In comparison, the group 2 implant was visible at both 3 and 6 weeks. The histology section for the group 2 implant showed significant cell infiltration and inflammation at 3 weeks post implantation. The inflammatory response decreased at 6 weeks and the implanted tissue region turned into fascia-like tissue at 6 weeks.

Figure 7:
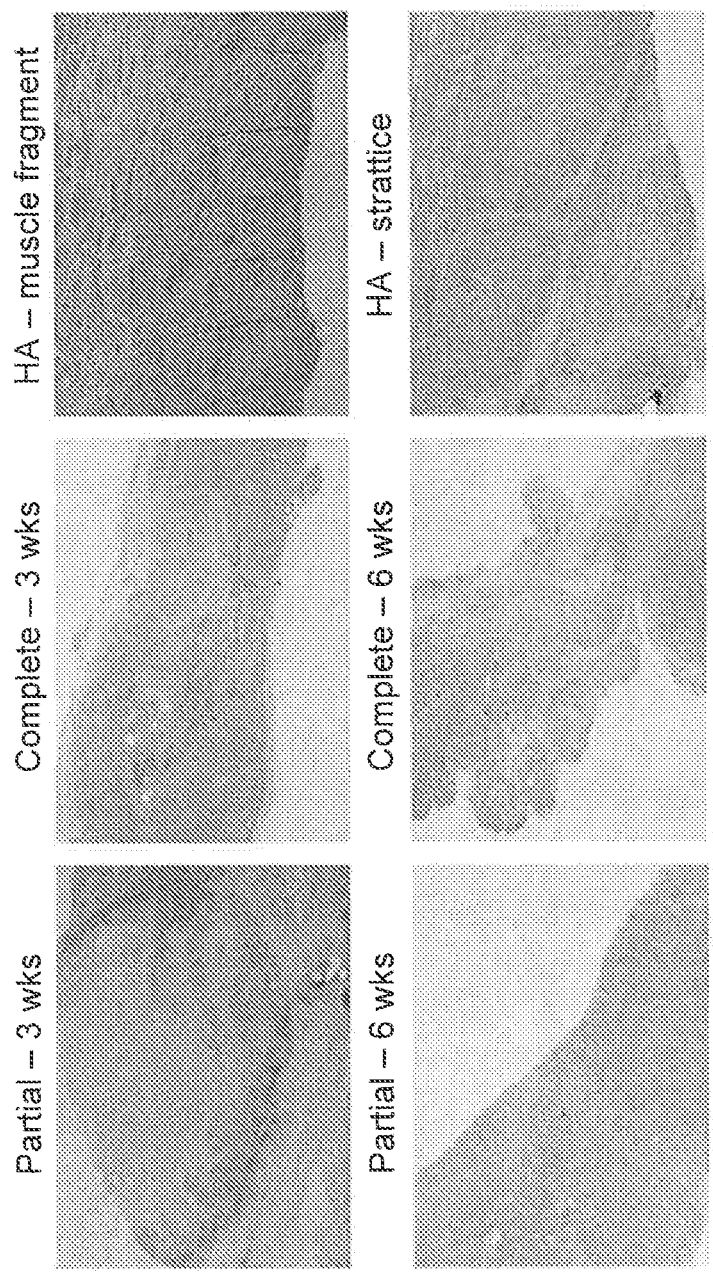
FIG. 7 shows H&E staining of sections of 1 $cm^2$ defects in rat skeletal muscle that were repaired using decellularized muscle having some retained myofiber (left column) and completely decellularized muscle (no myofiber retention) (center column), or using a mixture of hyaluronic acid and decellularized porcine muscle powder having some retained myofibers ("HA-muscle fragments," upper right), or using a mixture of hyaluronic acid and Strattice™ powder ("HA- Strattice," lower right). Sections were taken after 3 weeks and 6 weeks for the defects repaired with decellularized muscle having some retained myofibers and for the defects repaired with completely decellularized muscle. Sections were taken after 3 weeks for the defects repaired with HA-muscle fragments and HA-Strattice.

The defects repaired with HA-muscle fragments and HA-Strattice™ (groups 3 and 4) were only evaluated at the 3 week time point, when the decision was made that addition animal groups were unnecessary. With the HA-muscle fragment treatment, there were 2 cases of infection in the implanted tissue. The remaining rat treated with HA-muscle fragments experienced significant inflammation at 3 weeks, while the histological section revealed a large unfilled hole corresponding to the muscle defect. Gross observation of the tissue showed significantly thinner tissue where the muscle defect was created. The rats receiving the HA-Strattice™ fragment solution did not appear to retain the implant at the muscle defect site. There was significant cell infiltration around the injected solution, but only a limited amount of cell penetration into the core of the HA-Strattice™ solution matrix. FIG. 7 shows H&E staining for the different treatment groups at 3 weeks and 6 weeks post implantation.

Thus, of the different types of muscle/dermal-derived constructs evaluated in this study, a decellularized muscle graft that retains some myofibers appears to have outperformed the other testing arms. Without being bound by theory, the study results support the hypothesis that the retention of myofibers elicits appropriate levels of inflammation at the early stage of regeneration sufficient to induce complete muscle healing in 6 weeks. In contrast, the completely decellularized muscle matrix (no retained myofibers) failed to induce a similar level of regeneration and remained fascia-like at 6 weeks post implantation. The attempts to use an injectable approach did not yield desirable results in this report, as there were cases of infection and/or poor retention at the defect site. An alternative approach with a more gel-like (e.g., hydrogel) solution rather than a fluid-like solution may provide a greater chance of retention.

Example 4: Bilayer Implant

A bilayer implant comprising decellularized muscle and Strattice™ was created using fibrin glue to bind the layers together. The bilayer implant had a bonding strength of approximately IN and a bonding modulus of 31 kPa+/−20.1. Using the same fibrin glue method, it could be possible to stack multiple layers of decellularized muscle and/or Strattice™ to form a multilayer implant. In addition, bilayers were prepared by suturing together layers of Strattice™ and decellularized muscle.

The bilayer and multilayer implants can be implanted during abdominal hernia repair. After implantation, the degree of myogenesis and fibroblast infiltration is measured and compared to myogenesis and fibroblast infiltration in the absence of an implant or in the presence of an implant comprising intact muscle or fully decellularized tissue (e.g., decellularized tissue lacking any myofibers).

One benefit of using bilayer implants in abdominal wall and similar defects is that the dermal tissue in the implant can provide initial load bearing capacity, while over time the load bearing capacity is transferred to the muscle portion of the implant (which is initially weaker) as muscle regeneration progresses and the dermal tissue degrades. For example, a partial abdominal wall defect model was evaluated in rats using bilayer implants. Sections of rectus muscle (1.0×0.5 cm) were resected and filled with an implant containing either porcine acellular dermal matrix (PADM, Strattice™) or PADM sutured on top of one of two different decellularized and partially myofiber-removed muscle matrices (approximately 70% residual myofiber content or approximately 20% residual myofiber content). The implants were evaluated after 3 and 6 weeks.

Trichrome histology staining of the implants after three weeks demonstrated improved muscle regeneration in the bilayer implants, as compared to the PADM alone implant. After 6 weeks, substantial muscle regeneration was observed for both bilayer implants, with only minimal muscle regeneration observed in the PADM implant. Essentially normal muscle was observed in the bilayer implant containing 70% residual myofiber after six weeks, while the implant containing 20% residual myofiber exhibited slightly less complete regeneration.

The bilayer implant data confirms that these implants can induce skeletal muscle repair in a partial abdominal wall defect model, with approximately full regeneration observed after six weeks. The bilayer implants also reflect the tissue specificity of the muscle regeneration process—minimal muscle regeneration was observed in the PADM alone model, while more substantial muscle regeneration was observed in the bilayer implants. The data also demonstrates that the kinetic of muscle regeneration is related to the myofiber content of the implanted bilayer. Bilayer implants containing processed muscle tissue with approximately 70% myofiber content were able to induce faster muscle regeneration than the bilayers containing processed muscle tissue with approximately 20% residual myofiber content.

The preceding examples are intended to illustrate and in no way limit the present disclosure. Other embodiments of the disclosed devices and methods will be apparent to those skilled in the art from consideration of the specification and practice of the devices and methods disclosed herein.

What is claimed is:

1. A method of preparing an implant, the method comprising
   providing a muscle sample comprising natural myofibers; and
   processing the muscle sample to produce a decellularized muscle matrix retaining at least some of the natural myofibers, the processing comprising:
   contacting the muscle sample with a solution containing trypsin at a concentration of 0.1% to 0.5% w/v;
   decellularizing the muscle sample to produce the decellularized muscle matrix; and
   joining the decellularized muscle matrix to at least one decellularized dermal matrix to form a layered material comprising at least one decellularized muscle matrix layer and at least one decellularized dermal matrix layer in the form of a sheet.

2. The method of claim 1, wherein the muscle sample is decellularized by contacting the sample with a decellularization solution comprising at least one of 4-(1,1,3,3-Tetramethylbutyl)phenyl-polyethylene glycol, sodium dodecyl sulfate, sodium deoxycholate, and polyoxyethylene (20) sorbitan monolaurate.

3. The method of claim 1, wherein the decellularized muscle matrix retains about 20-80% of the natural myofibers present in the muscle sample.

4. The method of claim 1, further comprising contacting the muscle sample with DNase.

5. The method of claim 1, further comprising contacting the muscle sample with alpha-galactosidase.

6. The method of claim 1, wherein the muscle sample is from an animal that lacks substantially all alpha-galactose moieties.

7. The method of claim 1, wherein the at least one decellularized dermal matrix is at least two or at least three decellularized dermal matrices.

8. The method of claim 1, wherein the decellularized muscle matrix and the at least one decellularized dermal matrix are joined using a fibrin glue or sutures.

9. The method of claim 1, further comprising treating the decellularized muscle matrix to reduce bioburden.

10. The method of claim 9, wherein the decellularized muscle matrix is exposed to e-beam radiation.

11. The method of claim 1, further comprising packaging the layered material.

12. The method of claim 11, further comprising sterilizing the layered material.

* * * * *